United States Patent [19]

Schulz et al.

[11] Patent Number: 4,940,808
[45] Date of Patent: Jul. 10, 1990

[54] PROCESS FOR OZONIZATION OF UNSATURATED ORGANIC COMPOUNDS

[75] Inventors: Paul Schulz, Wuppertal, Fed. Rep. of Germany; Michael J. Virnig, Santa Rosa, Calif.; Franz J. Carduck, Haan, Fed. Rep. of Germany

[73] Assignee: Henkel Kommanditgesellschaft auf Aktien, Duesseldorf-Holthausen, Fed. Rep. of Germany

[21] Appl. No.: 216,067

[22] Filed: Jul. 7, 1988

[30] Foreign Application Priority Data

Jul. 8, 1987 [DE] Fed. Rep. of Germany ....... 3722566

[51] Int. Cl.$^5$ .................... C07D 317/54; C07C 55/14; C07C 51/31; C07C 61/04
[52] U.S. Cl. .................................... 549/436; 546/321; 546/327; 562/408; 562/421; 562/512.4; 562/544; 562/505; 568/469
[58] Field of Search ................ 568/469; 562/544, 421, 562/408, 505, 512.4; 549/436; 260/413 HC; 546/321, 327

[56] References Cited

U.S. PATENT DOCUMENTS

| | | | |
|---|---|---|---|
| 3,868,392 | 2/1975 | Siclari et al. | 562/544 |
| 4,185,025 | 1/1980 | Carduck et al. | 260/406 |
| 4,287,130 | 9/1981 | Dohm et al. | 562/544 |
| 4,613,694 | 9/1986 | Rossi et al. | 568/469 |

FOREIGN PATENT DOCUMENTS

| | | |
|---|---|---|
| 2713863 | 3/1977 | Fed. Rep. of Germany . |
| 3005514 | 2/1980 | Fed. Rep. of Germany . |

*Primary Examiner*—Nicky Chan
*Attorney, Agent, or Firm*—Ernest G. Szoke; Wayne C. Jaeschke; Henry E. Millson, Jr.

[57] ABSTRACT

A process for the ozonization of unsaturated organic compounds in a reaction column through which the unsaturated compounds—in solution in a protic solvent—and an ozone-containing carrier gas and an inert coolant are passed downward in co-current flow to provide for an improved coolant effect and an increased ozonization yield where the coolant comprises a compound gaseous or liquid at ambient temperature with a boiling point preferably in the range from +20° C. to −200° C. The boiling point of the coolant is preferably at least 5° C. below the ozonization temperature.

21 Claims, No Drawings

PROCESS FOR OZONIZATION OF UNSATURATED ORGANIC COMPOUNDS

BACKGROUND OF THE INVENTION

1. Field of the Invention

This invention relates to a process for ozonization of unsaturated organic compounds, more particularly olefins.

2. Discussion of Related Art

Processes for ozonization of unsaturated compounds in which internal cooling is effected by evaporative cooling using coolants boiling above the ozonization temperature, for example water or water-containing emulsions, are known from German Patent publications Nos. 27 13 863, 27 54 366 and 30 05 514. These processes have as one disadvantage that they are not suitable for the low temperature range, for example, ozonization processes which take place below $-10°$ C. (in the case of olefin components capable of entering into secondary reactions at relatively high temperatures). In addition, the evaporative cooling process presupposes that the ratio of ozone to carrier gas is not too high in order to guarantee the necessary evaporation or cooling capacity based on the ozone used (low ozone concentrations).

Low-temperature ozonizations of unsaturated compounds may be carried out, on a small scale, in cooled, jacketed columns with a suitable packing. However, reaction columns such as these involve high costs especially due to the additional heat exchange units required. Further disadvantages include the fact that even with an optimal column design in regard to residence time, a large part of the heat of reaction is released in a confined part of the column. "Stretching" of the reaction zones through the use of several inlets for olefin and ozone does not completely eliminate localized overheating. In prior processes, the scaling up of the reaction column presents considerable design problems on account of the increasing imbalance between the amount of heat to be dissipated and the available heat-exchange capacity; and unavoidable localized overheating resulting in yield losses.

The problems mentioned above are aggravated, in the case of evaporation cooling, by the fact that ozone generators which supply a carrier gas stream containing high concentrations of ozone, for example 100 g ozone per $m^3$ carrier gas, have recently become available.

DESCRIPTION OF THE INVENTION

Other than in the operating examples, or where otherwise indicated, all numbers expressing quantities of ingredients or reaction conditions used herein are to be understood as modified in all instances by the term "about".

According to this invention, the disadvantages mentioned above can be eliminated when carrying out an ozonization process in which the internal cooling is effected by evaporative cooling, by using a coolant which has a boiling temperature which is below the ozonization temperature in the column.

Accordingly, the present invention provides a process for ozonization of unsaturated organic compounds which comprises passing through a zone maintained under ozonization conditions a mixture containing an unsaturated organic compound, a protic solvent capable of dissolving the unsaturated organic compound and ozonization products thereof, an ozone containing material and a coolant to dissipate the heat of reaction which has a boiling point at least about 5° C. below the temperature maintained in said ozonization zone.

The coolant leaves the column (in the vapor phase) in the waste gas stream and, in one preferred embodiment of the invention, and be condensed by compression/cooling if its boiling point is not too low and returned to the process. Extremely low-boiling, inexpensive cooling components, such as liquid nitrogen, can be used also where economic considerations so dictate. In this case, no provision is made for recycling.

Accordingly, the process according to the invention preferably includes the employment of a coolant which is a compound gaseous or liquid at ambient temperature with a boiling point between $+20°$ C. and $-200°$ C., the boiling point of the coolant preferably being at least 5° C. below the ozonization temperature. The coolant used preferably boils at a temperature in the range from 10° to 30° C. below the ozonization temperature and, in addition, most preferably has boiling points between $+20°$ C. and $-100°$ C. and even more preferably between $-10°$ C. and $-50°$ C.

Preferred coolants used in the process of the invention include hydrocarbons, halogenated hydrocarbons, especially chlorinated and/or fluorinated methane or ethane, and dimethyl ether as well as carbon dioxide or liquid nitrogen. Particularly advantageous coolants are dichlorodifluoromethane and—particularly in the case of valuable reaction products, such as perfumes—liquid carbon dioxide.

In one advantageous embodiment of the invention, an inert carrier gas stream charged with ozone in a high concentration, which is produced by desorption of the ozone adsorbed on an inorganic material, for example silica gel, with the carrier gas, is used for ozonization. One such process for the production of ozone is described in German Patent publication No. 32 30 922.

In another advantageous embodiment of the invention, the coolant is introduced into an essentially vertical reaction column through a distributor nozzle at the head of the column while the mixture of unsaturated organic compounds and solvent as well as the ozone/carrier gas mixture are introduced downstream or beneath the coolant inlet.

The reaction mixture removed at the bottom of the reaction column is worked up in the conventional way into ozonization products; coolant and solvent can be returned to the process after appropriate purification where this is advisable on economic grounds.

To carry out the process of this invention, the olefin to be ozonized is preferably introduced into the column in a protic solvent, more particularly lower ($C_1$–$C_4$) alcohols or carboxylic acids, for example, methanol, ethanol, isopropanol. isobutanol, formic acid, acetic acid or propionic acid and the like, which are capable of dissolving both the starting olefin and also the ozonization products under the process conditions. At the same time, the ozone-containing carrier gas is passed through the column preferably in co-current flow. The evaporation coolant is preferably added above the inlet for olefin and ozone. The throughput is regulated in such a way that the reaction enthalpy is collected by evaporation and the temperature in the reaction column stabilizes at a predetermined desired value. As already mentioned, the phase removed at the bottom of the column is worked up in a conventional manner. The column may be cooled in addition by external cooling to a slight extent during the ozonization process to compensate for heat gain from the surrounding atmosphere.

The general conditions of the ozonization reaction itself and the further processing of the immediate ozonizaton products. e.g. by oxidative or reductive conversion are well known in the art (see e.g. L. Long, Jr.: The Ozonization Reaction, Chem. Revs. Vol. 27 (1927) pp. 437–493; P. S. Bailey: The Reactions of Ozone with Organic Compounds, Chem. Revs. Vol. 5 (1958) pp. 925–1010).

In the process of the invention the starting material can consist of any unsaturated organic compound know for its undergoing the reaction to ozone (see e.g. L. Long. Jr. loc. cit. and P. S. Bailey, loc. cit.). Thus, the process of the invention may be employed in the ozonization of the following species (in parenthisis the end products after oxidative conversion): cyclohexene (adipic acid), 1-octene (heptanoic acid), 1-dodecene (hendecanoic acid), oleylamine (omegaaminononanic acid), pinene (pinonic acid), naphthalene (phthalic acid), 8-hydroxyquinoline (quinolic acid), phenanthrene (diphenic acid), 1-dodecene (hendecanoic acid) and 1-tridecene (lauric acid) as well as the following species (in parenthesis end products after reductive conversion): cyclohexene (adipaldehyde), camphene (camphenilone), 1,2-dimethylcyclopentane (2,6-heptanedione), stilbene (benzaldehyde) anethole (anisaldehyde) and isoeugenole (vanillin).

The process of the invention is especially suitable for the ozonisation of compounds in the steroid and terpenoid series having an olefinically unsaturated side chain, e.g. for the ozonization of beta-pinene (yielding nopinone) or isosafrole (yielding heliotropin).

The process of the invention affords advantages including that it may readily be carried out in scaled-up form, the heat of reaction is dissipated from the reaction zone itself with elimination of overheating, yields obtained are higher than in the case of indirect cooling of the column, and fewer secondary products are formed.

The invention is illustrated by the following Examples.

EXAMPLE 1

4222 g/h 9% methanolic Isosafrol solution and 115 g/h ozone (in the form of approx. 1.1 m$^3$/h of an approx. 8% ozone/nitrogen mixture) were passed through a 2 mm×40 mm reaction column (fine steel; MELLAPACK packing). Above the inlet for the olefin solution approximately 6.5 kg/h dichlorodifluoromethane (Bp. −29.8° C.) as evaporation cooling medium were distributed throughout the column packing through a solid cone nozzle. The temperature was controlled through the throughput of coolant and was kept constant at around −10° C.

After catalytic-reductive working up of the ozonization product to heliotropin, a yield of approx. 85–90%, based on the Isosafrol used, was obtained.

Compression and cooling of the mixture of dichlorodifluoromethane, nitrogen and methanol in a single step produced a return flow of coolant which, besides the dichlorodifluoromethane, contained at most 5% methanol and could be directly returned to the reaction column.

EXAMPLE 2

380 g/h Isosafrol in the form of a 9% solution in methanol and 115 g/h (in the form of 8 m$^3$/h of an ozone/air mixture) were passed through the reaction column in co-current as in Example 1. For comparison purposes, this experiment was carried out in three ways:

A. With column jacket cooling (prior art).

The double jacket of the column was divided into four cooling zones through which cooling brine at −30° C. flowed. The throughput of coolant in each zone was regulated in such a way that the internal temperature of the column was −10° C. over the entire length of the column. 90% of the total cooling brine was used up in the olefin input zone.

B. With column jacket cooling and olefin input at four points of the column (prior art).

The four cooling zones were charged with the same throughput of coolant. The Isosafrol solution was distributed throughout the column packing via a distributor nozzle above the particular column section. At full cooling capacity, the olefin solution was thus distributed over the four inlets in such a way that the internal temperature of the column was at most −10° C. at each point of the column.

C. With internal evaporation cooling by liquid carbon dioxide (invention)

The Isosafrol solution was pumped in through a distributor nozzle in a quantity of 4.22 kg/h and distributed directly throughout the column packing. Above the olefin inlet, there was another distributor nozzle through which approx. 5.6 kg/h liquid carbon dioxide were introduced into the ozone/carrier gas stream. The liquid coolant was dosed in such a way that the temperature of the reaction zone (an approximately 25 cm long section of the column beyond the inlet for the reactants) settled at −10° C.

The temperature in the other zones of the column was also kept at −10° C. by gentle cooling with a cooling brine at −12° C. in the double jacket.

A carbon dioxide/methanol mixture containing approximately 1 to 3% methanol was condensed from the waste gas by compression and cooling and was returned to the cooling zone.

The following yields were obtained after catalytic-reductive working up to heliotropin:

version A: approx. 75%
version B: approx. 80%
version C: approx. 85–90%.

In version C (cooling with liquid carbon dioxide in accordance with the invention), the olefin/ozone throughput can be considerably increased in relation to versions A and B at a process temperature reliably kept constant at −10° C. in the described plant.

We claim:

1. A process for ozonization of an unsaturated organic compound which comprises: passing through a zone maintained under ozonization conditions a mixture containing an unsaturated organic compound, a protic solvent capable of dissolving the unsaturated organic compound and ozonization products thereof, an ozone containing material and a coolant having a boiling point in the range of from about +20° C. to about −200° C. to dissipate the heat of reaction which has a boiling point below the temperature maintained in said ozonization zone, and separating a stream containing ozonization product from said zone.

2. The process of claim 1 wherein said coolant comprises a hydrocarbon or halogenated hydrocarbon.

3. The process of claim 2 wherein said coolant is chlorinated methane or ethane or fluorinated methane or ethane.

4. The process of claim 1 in which the ozonization zone is maintained at an ozonization temperature up to about 40° C.

5. The process of claim 1 wherein the coolant has a boiling point in the range from about 10° C. to about 30° C. below the temperature maintained in said ozonization zone.

6. The process of claim 1 wherein said ozonization zone comprises an essentially vertical reaction column.

7. The process of claim 1 wherein said mixture is passed in cocurrent flow through said ozonization zone.

8. The process of claim 7 in which said mixture is passed downwardly in co-current flow.

9. The process of claim 1 wherein said ozone containing material comprises an inorganic material having ozone adsorbed thereon and desorbing ozone in said ozonization zone.

10. The process of claim 8 in which said coolant is introduced to the reaction column through a distribution zone at the head of said column and said unsaturated compound, solvent and ozone containing material are introduced downstream of said coolant.

11. The process of claim 1 in which said protic solvent comprises a lower alcohol.

12. The process of claim 11 in which said lower alcohol is a $C_1$–$C_4$ alcohol.

13. The process of claim 1 in which said protic solvent is a lower carboxylic acid.

14. The process of claim 13 in which said lower carboxylic acid is a $C_1$–$C_4$ carboxylic acid.

15. The process of claim 1 in which said coolant has a boiling point at least about 5° C. below the temperature maintained in the ozonization zone.

16. The process of claim 1 in which said mixture is introduced to the ozonization zone and product is separated on a substantially continuous basis.

17. The process of claim 1 wherein the coolant comprises liquid nitrogen.

18. The process of claim 1 wherein said coolant has a boiling point in the range from about +20° C. to about −100° C.

19. The process of claim 1 wherein said coolant has a boiling point in the range from about −10° C. to about −50° C.

20. The process of claim 1 wherein said coolant comprises dimethyl ether.

21. The process of claim 1 wherein said coolent comprises carbon dioxide.

* * * * *